United States Patent
Shimaru

(10) Patent No.: US 12,005,211 B2
(45) Date of Patent: Jun. 11, 2024

(54) METHOD FOR PRODUCING BALLOON CATHETER

(71) Applicant: KANEKA CORPORATION, Osaka (JP)

(72) Inventor: Masayasu Shimaru, Settsu (JP)

(73) Assignee: KANEKA CORPORATION, Osaka (JP)

( * ) Notice: Subject to any disclaimer, the term of this patent is extended or adjusted under 35 U.S.C. 154(b) by 511 days.

(21) Appl. No.: 17/437,639

(22) PCT Filed: Feb. 5, 2020

(86) PCT No.: PCT/JP2020/004424
§ 371 (c)(1),
(2) Date: Sep. 9, 2021

(87) PCT Pub. No.: WO2020/184004
PCT Pub. Date: Sep. 17, 2020

(65) Prior Publication Data
US 2022/0176086 A1 Jun. 9, 2022

(30) Foreign Application Priority Data
Mar. 14, 2019 (JP) .................................. 2019-047523

(51) Int. Cl.
*A61M 25/10* (2013.01)
(52) U.S. Cl.
CPC ..... *A61M 25/1029* (2013.01); *A61M 25/1034* (2013.01)
(58) Field of Classification Search
CPC ........................ A61M 25/1027; B29C 2049/48
See application file for complete search history.

(56) References Cited

U.S. PATENT DOCUMENTS 6,572,813 B1 * 6/2003 Zhang ..................... B29C 55/24
264/903
7,264,458 B2 * 9/2007 Holman .............. B29C 49/6445
264/458

(Continued)

FOREIGN PATENT DOCUMENTS

JP 10-33658 A 2/1998
JP 2005-518879 A 6/2005

(Continued)

OTHER PUBLICATIONS

International Search Report for PCT/JP2020/004424 mailed on Mar. 31, 2020.

*Primary Examiner* — Cachet I Proctor
(74) *Attorney, Agent, or Firm* — Birch, Stewart, Kolasch & Birch, LLP

(57) ABSTRACT

Provided is a method for producing a balloon catheter having a high-quality balloon, the method enabling an entire mold to be uniformly heated. A method for producing a balloon catheter having a shaft extending in a distal-proximal direction and a balloon provided on a distal side of the shaft, the method comprising: a tubular body placement step of placing a resin tubular body (10) inside a mold (20); a mold placement step of placing the mold (20) inside a heating jacket (30); a heating start step of starting heating the heating jacket (30); an elongation start step of starting elongating the resin tubular body (10) in a lengthwise direction thereof an elongation end step of ending elongating the resin tubular body (10); and a heating end step of ending heating the heating jacket (30), wherein the heating end step is performed before the elongation end step.

16 Claims, 7 Drawing Sheets

(56) References Cited

U.S. PATENT DOCUMENTS

| | | | |
|---|---|---|---|
| 2003/0167067 A1* | 9/2003 | Wang | B29C 48/09 |
| | | | 606/192 |
| 2006/0151921 A1 | 7/2006 | Wang et al. | |
| 2007/0088378 A1* | 4/2007 | Okushi | A61M 25/1029 |
| | | | 606/192 |
| 2012/0323301 A1 | 12/2012 | Wang et al. | |
| 2014/0330202 A1 | 11/2014 | Wang et al. | |
| 2015/0352335 A1* | 12/2015 | Moeller | A61L 29/103 |
| | | | 606/194 |
| 2018/0085499 A1 | 3/2018 | Wang et al. | |
| 2019/0151630 A1* | 5/2019 | Takeuchi | A61M 25/104 |

FOREIGN PATENT DOCUMENTS

| | | | |
|---|---|---|---|
| JP | 2008-23270 A | | 2/2008 |
| JP | 2008023270 A | * | 2/2008 |
| JP | 2017-63803 A | | 4/2017 |
| WO | WO 2018/047575 A1 | | 3/2018 |

* cited by examiner

[FIG. 1]
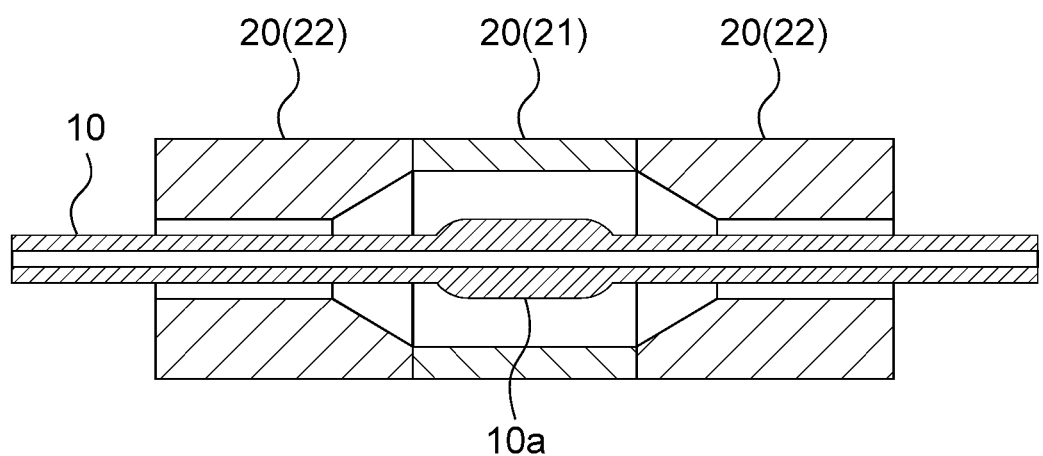

[FIG. 2]
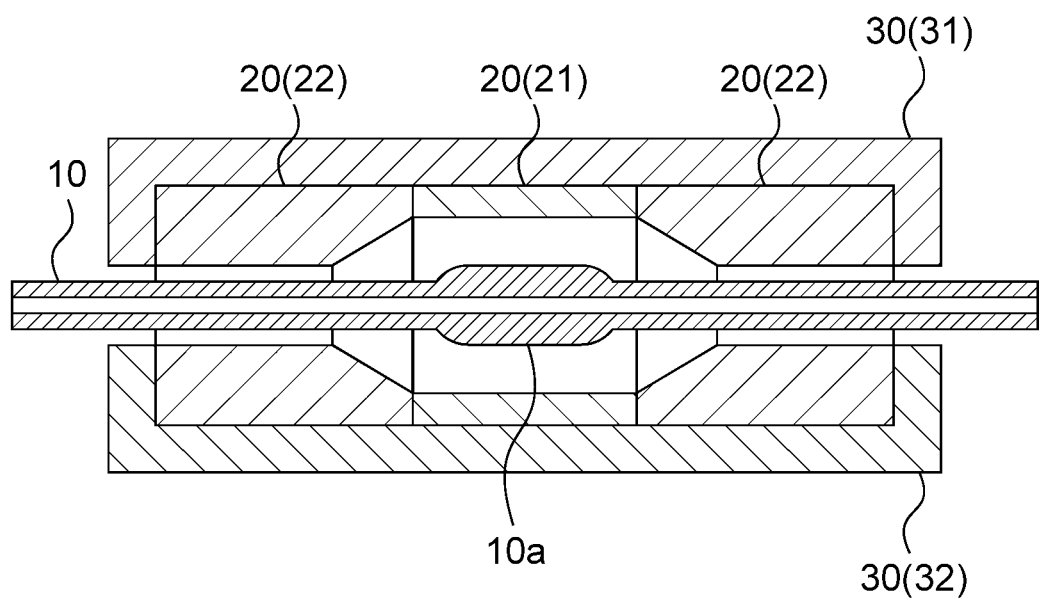

[FIG. 3]
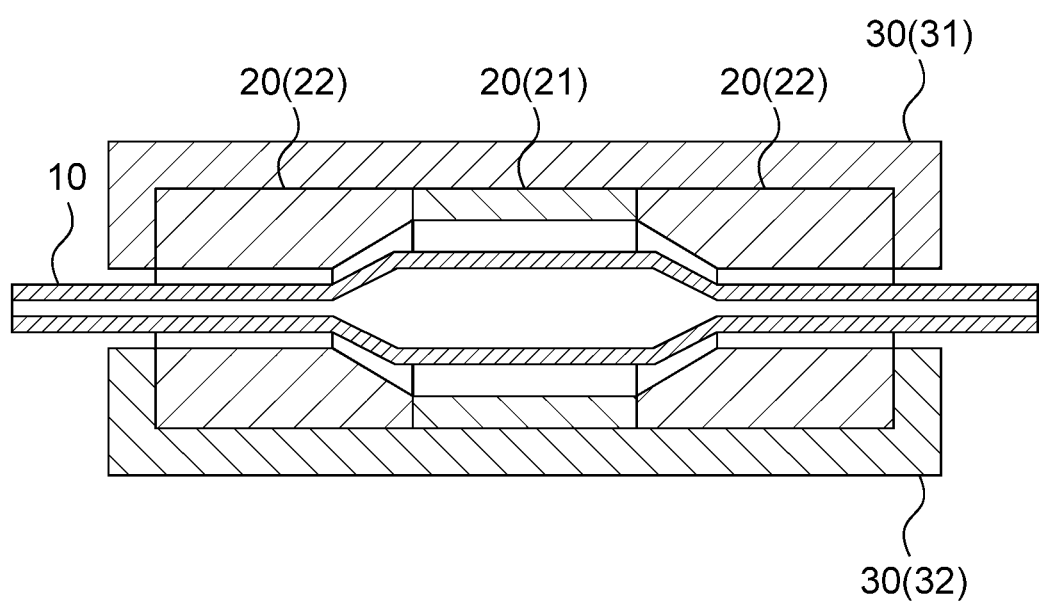

[FIG. 4]
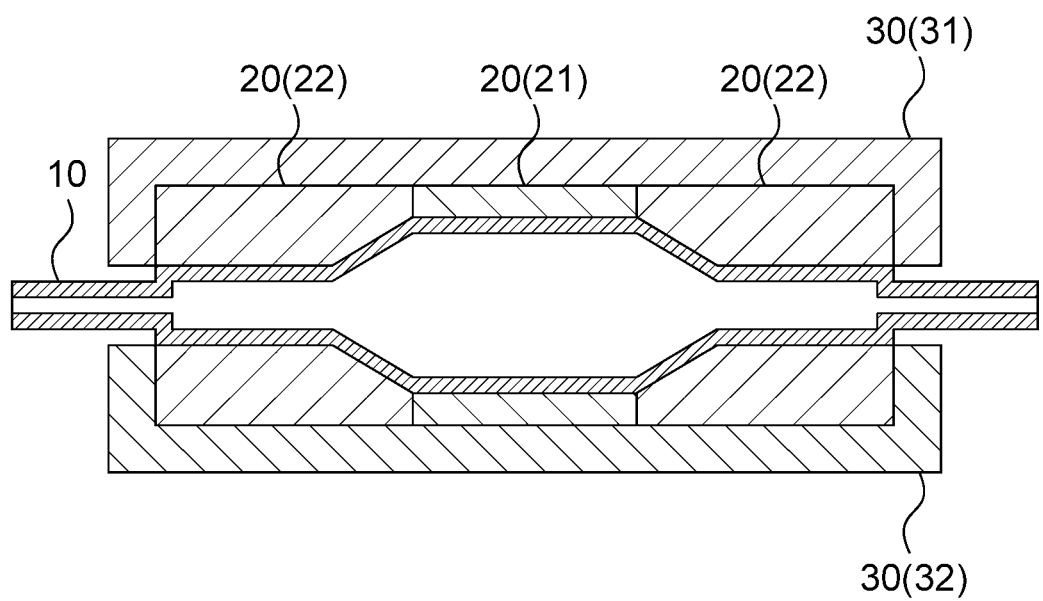

[FIG. 5]
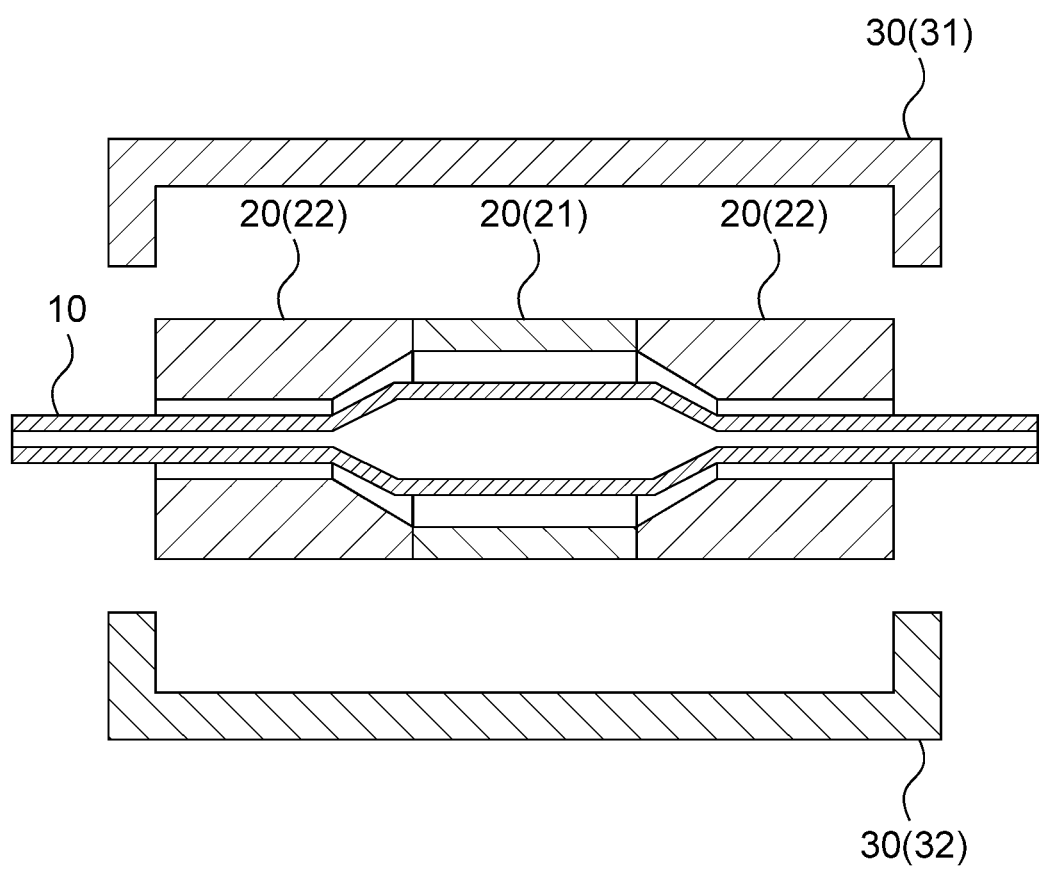

[FIG. 6]
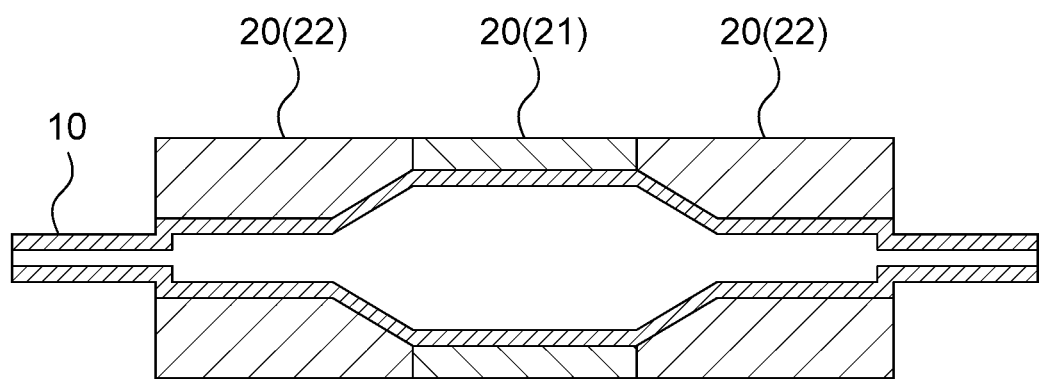

[FIG. 7]
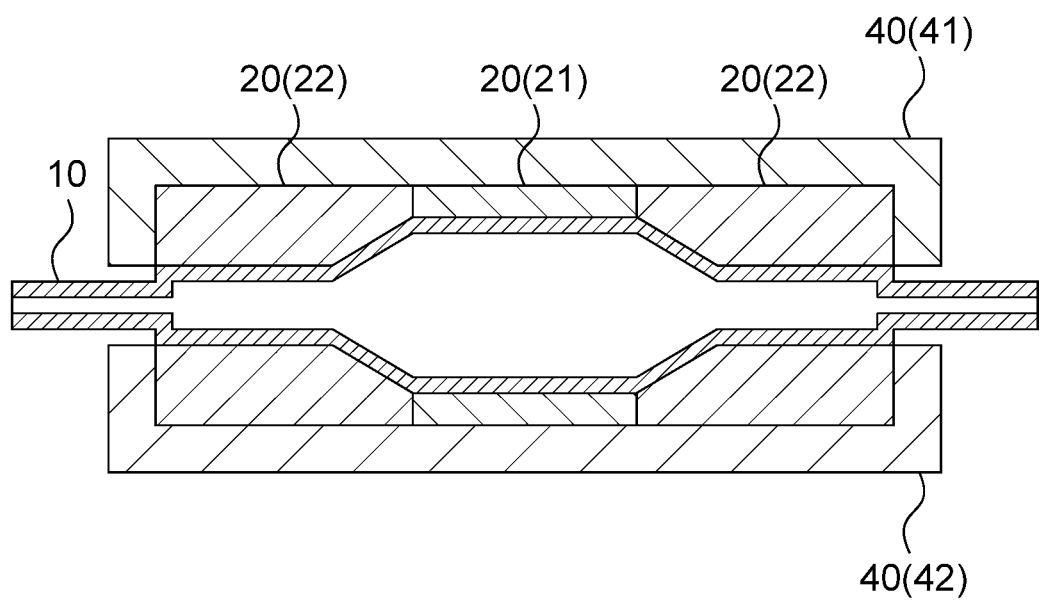

METHOD FOR PRODUCING BALLOON CATHETER

TECHNICAL FIELD

The present invention relates to a method for producing a balloon catheter having a balloon.

BACKGROUND ART

It has been known that various diseases are developed by stagnation in circulation of blood due to occurrence of a stenosis of a blood vessel which is a flow path for circulating blood in the body. Especially, if a coronary artery for supplying blood to the heart suffers a stenosis, critical diseases such as angina pectoris and myocardial infarction may be caused. As methods for treating such a stenosis site of a blood vessel, there are procedures for expanding the stenosis site by using a balloon catheter (for example, angioplasties such as PTA and PTCA). Angioplasties are minimally invasive therapies requiring no thoracotomies such as bypass surgery and are widely conducted.

For example, Patent Document 1 describes a method for producing a catheter balloon. The method includes: stretching both sides of a tubular parison in a predetermined proportion, to form a preparatory parison in a state where an unstretched portion having a predetermined width remains on a center portion thereof; mounting the preparatory parison inside a mold; heating the mold to a first molding temperature that is not lower than a secondary transition temperature and not higher than a primary transition temperature; causing a pressurization fluid to flow into the preparatory parison and subjecting the preparatory parison to primary stretch, to perform primary molding into a balloon shape that matches the shape of the inner surface of the mold and that has a balloon portion, tapered portions, and small-diameter connection portions; and thereafter, performing a step of heating the mold to a second molding temperature that is not lower than the first molding temperature and not higher than the primary transition temperature and a step of stretching both sides of the parison again, to perform secondary molding in which the tapered portions and the connection portions are thinned. Patent Document 1 further indicates that: the mold is configured to be integrally heated from the periphery thereof by a heat means; and, if the heat means is divided into three means to be composed of a balloon portion heating means and end portion heating means, the temperatures of the balloon portion, the tapered portions, and the connection portions of the parison can each be independently controlled.

Patent Document 2 describes a method for producing a medical balloon. The method includes: a parison forming step of forming a parison; and a blow molding step of blow molding the parison with a mold. The blow molding step includes: inserting the parison formed by the parison forming step into a separation type mold having a heater as a heating means and a cooling tube as a cooling means which are placed on the outer side of the mold; performing heating and pressurization in a state where both ends are sealed and an internal pressure is applied; stretching the parison in a direction in which the parison extends; inflating, by an internal pressure, the parison at a portion thereof being heated in the mold, the inflation being performed such that the parison comes into close contact with a separation type inner wall surface, to mold the parison into a balloon shape; performing annealing treatment with the parison being retained for a certain time while an internal pressure is being applied at a temperature that is not lower than a molding temperature and not higher than the melting point of a polymer, to achieve shape memorization; and thereafter, cooling the parison to normal temperature.

Patent Document 3 describes a method for producing a balloon placed in a medical catheter. The method includes a molding step of performing blow molding on a tubular parison made from a birefringent macromolecular material, to mold an expandable tubular portion of a balloon. The molding step includes: a first stretch step of stretching the tubular parison in an axial direction at normal temperature in a state where a pressure is applied into the tubular parison; and a second stretch step of stretching, in the axial direction, the tubular parison heated after the first stretch step, and meanwhile, swelling the tubular parison by a pressure applied into the tubular parison.

Patent Document 4 describes a balloon forming method in which: preceding radial inflation of an extruded parison, preparatory stretch may be performed in a longitudinal direction by various methods before inflation or re-formation in order to reduce the thicknesses of a cone portion and a waist portion of a balloon; in a subsequent blowing step, rapid immersion into a heated fluid may be performed with use of pressurization during elongation or successive immersions into the heated fluid may be performed at different pressures, and vibration and pressurization may be performed with a compressible or incompressible fluid after a material is heated; and the heating may be achieved by heating a pressurization fluid supplied into the parison. Patent Document 4 further indicates, in relation to blow molding temperature and pressure, that the balloon after blow molding may be simply cooled, may be heat set at a higher pressure and/or temperature, or may be heat shrunk at an intermediate pressure and/or temperature.

Patent Document 5 describes a method for producing an expanding catheter. The method includes: molding an original tube from a straight-chain low-density polyethylene resin; crosslinking the original tube, to make a crosslinked tube; stretching the crosslinked tube by blow molding, to make a balloon; and mounting the balloon to a catheter, to produce an expanding catheter. Patent Document 5 further indicates that: the crosslinked tube is inserted into a balloon molding mold (blowing mold) having a cavity with a desired outer diameter dimension and is set in a blow molding machine, the temperature is increased to an appropriate temperature, and then the crosslinked tube is stretched in a longitudinal direction and shaped into a balloon shape by blow pressurization; the longitudinal stretch step and the blowing step can be performed in succession in the same mold; the temperatures for both steps can be set to the same level; and longitudinal stretch of the crosslinked tube is performed as a step preceding blow molding of the crosslinked tube, and blow molding may be performed immediately after the stretch of the crosslinked tube or may be performed after the elapse of a certain time.

PRIOR ART DOCUMENTS

Patent Documents

Patent Document 1: JP 2008-23270 A
Patent Document 2: WO 2018/47575
Patent Document 3: JP 2017-63803 A
Patent Document 4: JP 2005-518879 A
Patent Document 5: JP H10-33658 A

SUMMARY OF INVENTION

Problems to be Solved by the Invention

In each of the methods for producing balloon catheters as in Patent Documents 1 to 5, a jacket having a heater block (cartridge heater) is ordinarily placed on the outer side of the mold for molding a balloon. In a general method for producing a balloon, a heater block of a jacket is energized first, and the temperature of the jacket is increased to heat a mold. Next, when the temperature of the jacket reaches a target temperature, energization of the heater block is canceled and temperature increase of the jacket is stopped to interrupt heating of the mold. Accordingly, the temperature of the mold is controlled. Then, a resin tubular body placed inside the mold is machined to produce a balloon. However, such a method in which the temperature is controlled by ON or OFF of energization of the heater block leads to occurrence of significant non-uniformity in the temperature of the mold, whereby it is difficult to uniformly heat the entire mold. As a result, non-uniformity in temperature occurs also in the resin tubular body placed inside the mold, and problems arise in that: the thickness of the molded balloon is not uniform; and the balloon is bent.

In addition, since both the jacket having the heater block and the mold are each made of a rigid material such as metal, there are both a portion at which the jacket and the mold are in direct contact with each other and a portion at which the jacket and the mold are distant from each other and thus an air space is present between the jacket and the mold. Since the extent of contact between the jacket and the mold and the distance between the jacket and the mold are also different depending on each location, the manner of transmission of heat from the jacket to the mold is not uniform, and thus a problem arises in that it is difficult to uniformly heat the entire mold.

Further, the jacket has a plurality of heater blocks, and there is an individual difference in heating performance among the heater blocks, and in addition, the extent of degradation is also different among the heater blocks. Thus, the temperature of a portion of the mold that faces a heater block having a high heating performance easily rises, whereas the temperature of a portion of the mold that faces a heater block having a low heating performance does not easily rise. As a result, non-uniformity in the temperature of the entire mold easily occurs, and thus a problem arises in that it is difficult to mold a balloon that has a uniform thickness and that is not bent.

The present invention has been made in view of the aforementioned circumstances, and an object of the present invention is to provide a method for producing a balloon catheter having a high-quality balloon, the method enabling an entire mold to be uniformly heated.

Solutions to the Problems

A first method for producing a balloon catheter of the present invention that has solved the above problems comprising: a method for producing a balloon catheter having a shaft extending in a distal-proximal direction and a balloon provided on a distal side of the shaft, the method comprising: a tubular body placement step of placing a resin tubular body inside a mold; a mold placement step of placing the mold inside a heating jacket; a heating start step of starting heating the heating jacket; an elongation start step of starting elongating the resin tubular body in a lengthwise direction thereof; an elongation end step of ending elongating the resin tubular body; and a heating end step of ending heating the heating jacket, wherein the heating end step is performed before the elongation end step.

The method for producing a balloon catheter is preferable wherein the heating end step is performed before the elongation start step.

The method for producing a balloon catheter is preferable further comprising a heating restart step of restarting heating the heating jacket, the heating restart step being performed after the heating end step.

A second method for producing a balloon catheter of the present invention that has solved the above problems comprising: a method for producing a balloon catheter having a shaft extending in a distal-proximal direction and a balloon provided on a distal side of the shaft, the method comprising: a tubular body placement step of placing a resin tubular body inside a mold; a mold placement step of placing the mold inside a heating jacket; a heating start step of starting heating the heating jacket; an elongation start step of starting elongating the resin tubular body in a lengthwise direction thereof; an elongation end step of ending elongating the resin tubular body; and a detaching step of detaching the mold from the heating jacket, wherein the detaching step is performed before the elongation end step.

The method for producing a balloon catheter is preferable wherein the detaching step is performed before the elongation start step.

The method for producing a balloon catheter is preferable further comprising: a mold re-placement step of placing the mold inside the heating jacket, the mold re-placement step being performed after the detaching step; and a heating restart step of restarting heating the heating jacket, the heating restart step also being performed after the detaching step.

The method for producing a balloon catheter is preferable wherein a difference between a temperature of the heating jacket at an end of the detaching step and a temperature of the heating jacket at a start of the mold re-placement step is not higher than 100° C.

The method for producing a balloon catheter is preferable wherein the difference between the temperature of the heating jacket at the end of the detaching step and the temperature of the heating jacket at the start of the mold re-placement step is not higher than 10° C.

The method for producing a balloon catheter is preferable wherein the heating jacket includes a plurality of partial heating jackets.

The method for producing a balloon catheter is preferable wherein the heating jacket includes a first partial heating jacket located closer to one side surface of the mold, and a second partial heating jacket located closer to another side surface of the mold, and the detaching step includes separating at least one of the first partial heating jacket and the second partial heating jacket from the mold.

The method for producing a balloon catheter is preferable wherein the first partial heating jacket and the second partial heating jacket are connected to each other via a hinge portion.

The method for producing a balloon catheter is preferable wherein the heating jacket includes a first partial heating jacket located closer to one end of the mold, and a second partial heating jacket located closer to another end of the mold, and the detaching step includes separating at least one of the first partial heating jacket and the second partial heating jacket from the mold.

The method for producing a balloon catheter is preferable wherein the heating start step is performed before the mold placement step.

The method for producing a balloon catheter is preferable further comprising a step of placing the mold inside a cooling jacket, the step being performed after the elongation end step of ending elongating the resin tubular body.

Effects of the Invention

According to the balloon catheter production method of the present invention, before elongation of the resin tubular body placed inside the mold to both sides in the lengthwise direction of the resin tubular body is ended, heating of the heating jacket is ended or the mold is detached from the heating jacket, whereby heat can be stopped from being supplied from the heating jacket to the mold. Consequently, the temperature of the entire mold easily becomes uniform owing to heat conduction of the mold itself. That is, the resin tubular body is elongated in a state where the temperature of the entire mold is uniform. Therefore, the resin tubular body placed inside the mold is less likely to suffer non-uniformity in temperature, whereby it is possible to mold a balloon catheter having a balloon that has a uniform thickness and that is less likely to be bent.

BRIEF DESCRIPTION OF THE DRAWINGS

FIG. 1 is a step cross-sectional view of a tubular body placement step in an embodiment of the present invention.

FIG. 2 is a step cross-sectional view of a mold placement step in the embodiment of the present invention.

FIG. 3 is a step cross-sectional view of an elongation start step in the embodiment of the present invention.

FIG. 4 is a step cross-sectional view of an elongation end step in the embodiment of the present invention.

FIG. 5 is a step cross-sectional view of a detaching step in another embodiment of the present invention.

FIG. 6 is a step cross-sectional view of an elongation end step in the other embodiment of the present invention.

FIG. 7 is a step cross-sectional view of a step of placing a mold inside a cooling jacket, in each of the embodiments of the present invention.

MODE FOR CARRYING OUT THE INVENTION

Hereinafter, the present invention will be more specifically described based on the following embodiments. However, the present invention is not limited to the following embodiments and, as a matter of course, can also be carried out with appropriate modifications being made within the scope of the gist described above and below, and any of these modifications are included in the technical scope of the present invention. In any of the drawings, hatching, reference characters for members, or the like may be omitted for convenience. In this case, see the description and the other drawings. Since priority is given to facilitating the understanding of the characteristics of the present invention, the dimensions of various members in the drawings may be different from actual dimensions.

FIG. 1 to FIG. 3 and FIG. 7 are step cross-sectional views of respective steps of a first production method and a second production method for a balloon catheter in embodiments of the present invention. FIG. 4 is a step cross-sectional view of an elongation end step in the first production method for the balloon catheter. FIG. 5 and FIG. 6 are step cross-sectional views of steps in the second production method for the balloon catheter. FIG. 7 is a step cross-sectional view of a step of placing a mold inside a cooling jacket, in each of the first and second production methods for the balloon catheter.

A balloon of the balloon catheter in the present invention can be produced by applying a pressure into a resin tubular body 10, heating the resin tubular body 10, and stretching the resin tubular body 10 in a lengthwise direction. Specifically, the balloon can be produced by performing blow molding on the resin tubular body 10. In production of the balloon, a pressure may be applied to the inside before stretch of the resin tubular body 10, may be applied to the inside simultaneously with the stretch, or may be applied to the inside during the stretch or after the stretch. In particular, the resin tubular body 10 is preferably stretched in the lengthwise direction in a state where a pressure is applied into the resin tubular body 10. If the balloon is produced by stretching the resin tubular body 10 in the lengthwise direction in a state where a pressure is applied into the resin tubular body 10, production efficiency for the balloon catheter can be improved.

As shown in FIG. 1 to FIG. 4, the first production method for the balloon catheter of the present invention includes: a tubular body placement step of placing a resin tubular body 10 inside a mold 20; a mold placement step of placing the mold 20 inside a heating jacket 30; a heating start step of starting heating the heating jacket 30; an elongation start step of starting elongating the resin tubular body 10 to both sides in a lengthwise direction thereof an elongation end step of ending elongating the resin tubular body 10; and a heating end step of ending heating the heating jacket 30, wherein the heating end step is performed before the elongation end step.

As shown in FIG. 1, in the tubular body placement step, the resin tubular body 10 is placed inside the mold 20. The resin tubular body 10 is a tubular object made of a synthetic resin, and is a so-called parison for use in blow molding. The mold 20 has therein a space with the same shape as the external shape of the balloon, and the resin tubular body 10 is placed in this internal space.

The material of the resin tubular body 10 is preferably a thermoplastic resin. Examples of the material of the resin tubular body 10 include: polyolefin-based resins such as polyethylene, polypropylene, and ethylene-propylene copolymer; polyester-based resins such as polyethylene terephthalate and polyester elastomer; polyurethane-based resins such as polyurethane and polyurethane elastomer; polyphenylene sulfide-based resins; polyamide-based resins such as polyamide and polyamide elastomer; vinyl chloride-based resins; fluorine-based resins; silicone-based resins; natural rubbers such as latex rubber; and the like. Only one type of these materials may be used, or two or more types of these materials may be used in combination. Among these materials, a polyamide-based resin, a polyester-based resin, or a polyurethane-based resin is suitably used as the material of the resin tubular body 10. Especially, an elastomer resin is preferably used in terms of the thickness reduction and the flexibility of the balloon. Examples of a material suitable for the resin tubular body 10 among the polyamide-based resins include nylon 12, nylon 11, and the like, and nylon 12 is suitably used in that nylon 12 enables relatively easy molding at the time of blow molding. Further, a polyamide elastomer such as polyether ester amide elastomer or polyamide ether elastomer is preferably used in terms of the thickness reduction and the flexibility of the balloon. Among these materials, polyether ester amide elastomer is preferably used in that polyether ester amide elastomer has a high yield strength and allows the balloon to have a favorable dimensional stability.

The length in the lengthwise direction of the resin tubular body 10 is preferably larger than the length of the internal space of the mold 20. That is, as shown in FIG. 1, both end portions of the resin tubular body 10 is preferably exposed from the mold 20 in a state where the resin tubular body 10 is placed inside the mold 20. Since the resin tubular body 10 has such a form, the elongation start step subsequent to the tubular body placement step is easily performed, whereby production efficiency for the balloon catheter can be improved.

The length in the lengthwise direction of the resin tubular body 10 is preferably not smaller than 1.05 times, more preferably not smaller than 1.10 times, and further preferably not smaller than 1.15 times the length of the internal space of the mold 20. If the lower limit value of the ratio of the length in the lengthwise direction of the resin tubular body 10 to the length of the internal space of the mold 20 is thus set, it is possible to elongate the resin tubular body 10 to both sides in the lengthwise direction thereof while sufficiently gripping both end portions of the resin tubular body 10 in the elongation start step. Thus, it becomes easy to perform the elongation start step. Meanwhile, the upper limit value of the ratio of the length in the lengthwise direction of the resin tubular body 10 to the length of the internal space of the mold 20 can be set as follows, for example. That is, the length in the lengthwise direction of the resin tubular body 10 can be set to be not larger than 100 times, not larger than 90 times, not larger than 80 times, or not larger than 70 times the length of the internal space of the mold 20.

The thickness of the resin tubular body 10 can be set according to the thickness of the balloon. The thickness can be set to be, for example, not larger than 3 mm, not larger than 2 mm, or not larger than 1 mm, and meanwhile, not smaller than 0.05 mm, not smaller than 0.07 mm, or not smaller than 0.1 mm.

The resin tubular body 10 preferably has a larger-thickness portion 10a having a larger thickness than the other portion thereof. If the larger-thickness portion 10a is located at a portion expandable to have a large outer diameter such as a straight tube portion or a tapered portion of the balloon, the thickness of the balloon can be sufficiently ensured. Thus, the durability of the balloon can be improved.

The resin tubular body 10 can be made by, for example, extrusion, injection molding, or the like. In particular, the resin tubular body 10 is preferably produced by extrusion. That is, a step of making the resin tubular body 10 by extrusion is preferably included, the step being performed before the tubular body placement step. If the resin tubular body 10 is made by extrusion, a large amount of the resin tubular body 10 can be made in a short time. Therefore, production efficiency for the balloon catheter can be improved.

The mold 20 preferably has a plurality of partial molds. Specifically, the mold 20 preferably has, for example, a center portion mold 21 which forms a straight tube portion at a center portion of the balloon and end portion molds 22 which are located on both sides of the center portion mold 21 and which form tapered portions located at both ends of the straight tube portion of the balloon. If the mold 20 has the plurality of partial molds, various shapes of balloons can be produced according to the purpose by replacing the center portion mold 21 or the end portion molds 22.

The material of the mold 20 is preferably a metal and more preferably iron, copper, aluminum, or an alloy thereof. Examples of the alloy of iron include stainless steel and the like. Examples of the alloy of copper include brass and the like. Examples of the alloy of aluminum include duralumin and the like. If the material of the mold 20 is iron, copper, aluminum, or an alloy thereof, the mold 20 has a high heat capacity and a high heat transfer property. Thus, the temperature of the entire mold 20 is easily set to a fixed level, the resin tubular body 10 placed inside the mold 20 is less likely to suffer non-uniformity in temperature, and it becomes easy to produce a balloon.

As shown in FIG. 2, in the mold placement step, the mold 20 is placed inside the heating jacket 30. The heating jacket 30 is used for applying heat to the mold 20.

The mold placement step may be performed before the tubular body placement step but is preferably performed after the tubular body placement step. If the mold placement step is performed after the tubular body placement step in production of the balloon, the resin tubular body 10 is easily placed inside the mold 20, whereby production efficiency for the balloon can be improved.

In the heating start step, heating of the heating jacket 30 is started. After the heating start step, the heating jacket 30 is heated to a preset temperature to apply the heat from the heating jacket 30 to the mold 20, so that the resin tubular body 10 placed inside the mold 20 is heated.

The temperature of the heating jacket 30 is preferably higher than a heating target temperature of the mold 20. If the temperature of the heating jacket 30 is set to be higher than the heating target temperature of the mold 20, it becomes easy to efficiently increase the temperature of the mold 20 to the heating target temperature.

The lower limit value of the temperature of the heating jacket 30 is preferably a temperature equal to the heating target temperature of the mold 20, more preferably a temperature higher by 5° C. than the heating target temperature of the mold 20, further preferably a temperature higher by 10° C. than the heating target temperature, even more preferably a temperature higher by 15° C. than the heating target temperature, and particularly preferably a temperature higher by 20° C. than the heating target temperature. If the lower limit value of the temperature of the heating jacket 30 is set to fall within the above range, the temperature of the mold 20 can be increased to the heating target temperature in a short time. Meanwhile, the upper limit value of the temperature of the heating jacket 30 is preferably a temperature higher by 250° C. than the heating target temperature of the mold 20, more preferably a temperature higher by 225° C. than the heating target temperature, and further preferably a temperature higher by 200° C. than the heating target temperature. If the upper limit value of the temperature of the heating jacket 30 is set to fall within the above range, it becomes easy to adjust the temperature of the mold 20.

The heating start step may be performed after the mold placement step but is preferably performed before the mold placement step. If the heating start step is performed before the mold placement step, the temperature of the heating jacket 30 has already reached the preset value at the time of performing the mold placement step. Thus, the mold 20 can be swiftly heated.

The heat dissipation rate of the mold 20 is preferably not higher than 30%, more preferably not higher than 10%, and further preferably not higher than 1%. The heat dissipation rate of the mold 20 can be obtained by an expression of (heat dissipation amount (J)/heat accumulation amount (J))×100. The heat accumulation amount is the amount of heat retained by the mold 20 having been heated to a certain temperature and is determined according to the material and the mass of the mold 20. The heat dissipation amount is the amount of heat lost from the mold 20 until 30 seconds after: energization of the heating jacket 30 is ended; or the heating jacket 30 is detached from the mold 20. The heat dissipation amount is determined according to the material, the mass, the shape (surface area), the temperature, and the ambient temperature of the mold 20. The temperature of the mold 20 is reduced from the surface thereof. Thus, if the upper limit value of the heat dissipation rate of the mold 20 is set to fall within the above range, the temperature of the center portion, of the mold 20, that is profoundly related to production of the balloon is less likely to be reduced. Consequently, the heat retaining property of the mold 20 is improved. Therefore, the resin tubular body 10 placed inside the mold 20 is less likely to suffer non-uniformity in temperature, whereby it becomes easy to produce a balloon that has a uniform thickness and that is less likely to be bent.

As shown in FIG. 3, in the elongation start step, elongation of the resin tubular body 10 in the lengthwise direction thereof is started. The resin tubular body 10 is preferably elongated to both sides in the lengthwise direction thereof. Examples of a method for elongating the resin tubular body 10 to both sides in the lengthwise direction thereof include: a method in which both end portions of the resin tubular body 10 are gripped and each of both end portions is pulled so that the resin tubular body 10 is elongated to both sides in the lengthwise direction thereof; and the like.

In a state where the temperature of the mold 20 has reached the heating target temperature before the elongation start step, the amount of heat (J) of the heating jacket 30 is preferably not smaller than 1.1 times, more preferably not smaller than 3 times, and further preferably not smaller than 5 times the amount of heat (J) of the mold 20. If the lower limit value of the ratio of the amount of heat of the heating jacket 30 to the amount of heat of the mold 20 is set to fall within the above range, the amount of heat of the heating jacket 30 can be made sufficiently larger than the amount of heat of the mold 20. Consequently, when the mold 20 is placed inside the heating jacket 30, reduction in the temperature of the heating jacket 30 can be suppressed. As a result, the time taken to increase the temperature of the mold 20 can be shortened. Meanwhile, the upper limit value of the ratio of the amount of heat of the heating jacket 30 to the amount of heat of the mold 20 can be set as follows, for example. That is, the amount of heat of the heating jacket 30 can be set to be not larger than 300 times, not larger than 200 times, or not larger than 100 times the amount of heat of the mold 20.

When the resin tubular body 10 is elongated to a desired length after the elongation start step, elongation of the resin tubular body 10 is ended in the elongation end step as shown in FIG. 4.

A step of applying a pressure into the resin tubular body 10 may be performed before the elongation start step, after the elongation start step, simultaneously with the elongation start step, simultaneously with the elongation end step, or after the elongation end step. Examples of a method for applying a pressure into the resin tubular body 10 include: a method in which one end portion of the resin tubular body 10 is sealed, and a fluid such as air, nitrogen, or water is sent into the resin tubular body 10 from the other end portion thereof; a method in which the fluid is sent into the resin tubular body 10 from both end portions of the resin tubular body 10; and the like. In particular, the step of applying a pressure into the resin tubular body 10 is preferably performed before the elongation start step. If the step of applying a pressure into the resin tubular body 10 is performed to produce a balloon, the resin tubular body 10 can be sufficiently pressed against the inner surface of the mold 20, whereby the outer appearance quality of the balloon can be improved.

In the heating end step, heating of the heating jacket 30 is ended. Specifically, examples of the manner of performing this step include: a manner in which energization of the heating jacket 30 is stopped, to end heating the heating jacket 30; and the like. The heating end step is performed before the elongation end step. If the heating end step is performed before the elongation end step, supply of heat from the heating jacket 30 to the mold 20 is ended during elongation of the resin tubular body 10. Consequently, the mold 20 is less likely to be influenced by the temperature of a heater block heating the heating jacket 30, the temperature of the entire mold 20 becomes uniform owing to heat conduction of the mold 20 itself, and non-uniformity in temperature is less likely to occur. As a result, the balloon produced with the mold 20 has a uniform thickness and is less likely to be bent.

The heating end step is performed before the elongation end step, and the heating end step is preferably performed before the elongation start step. That is, the elongation start step and the elongation end step are preferably performed after the heating end step is ended. If the heating end step is performed before the elongation start step to produce a balloon, the temperature of the entire mold 20 not having yet been subjected to the elongation start step can be made uniform, and non-uniformity in temperature is further less likely to occur. Thus, the quality of the balloon can be improved.

A heating restart step of restarting heating the heating jacket 30 is preferably included, the heating restart step being performed after the heating end step. If the molded balloon is heated again after the heating treatment step, annealing treatment for removing residual stress from the balloon can be performed, whereby physical properties of the balloon can be stabilized.

It is preferable to, in the heating restart step, heat the heating jacket 30 to a temperature higher than the heating target temperature of the heating jacket 30 in the heating start step. If, in the heating restart step, the heating jacket 30 is heated to a temperature higher than the heating target temperature of the heating jacket 30 in the heating start step, the annealing treatment for the balloon can be efficiently performed, whereby a balloon having high dimensional stability and physical stability can be produced.

It is preferable to, in the heating restart step, heat the heating jacket 30 to heat the mold 20 to the target temperature and keep the mold 20 at the target temperature for a certain time in order to perform the annealing treatment for the balloon, and then perform a re-heating end step of ending heating the heating jacket 30. If, in the balloon production method, the mold 20 is heated to the target temperature and the mold 20 is kept at the target temperature for a certain time and then the re-heating end step is performed, the annealing treatment for the balloon can be sufficiently performed.

It is also preferable to, in the heating restart step, heat the heating jacket 30 to heat the mold 20 to the target temperature, then perform the re-heating end step of ending heating the heating jacket 30, then keep the mold 20 at the target temperature for a certain time, and perform annealing treatment for the balloon. If the mold 20 is heated to the target temperature and then the re-heating end step is performed and the mold 20 is kept at the target temperature for a certain time, supply of heat from the heating jacket 30 to the mold 20 is ended. Therefore, the temperature of the entire mold 20 becomes uniform owing to heat conduction of the mold 20 itself, and non-uniformity in temperature is less likely to occur.

The heating restart step is preferably performed after the heating end step and more preferably performed after the elongation end step. If the heating restart step is performed after the elongation end step, the annealing treatment for the balloon can be more efficiently performed, whereby a balloon having stable physical properties can be produced.

A step of applying a pressure into the resin tubular body 10 may be performed in the heating restart step. In a case where the step of applying a pressure into the resin tubular body 10 has already been performed before, after, or simultaneously with the aforementioned elongation start step, and simultaneously with or after the aforementioned elongation end step, a pressure lower than the pressure applied into the resin tubular body 10 in each of these steps is preferably applied in the heating restart step. If the step of applying the pressure into the resin tubular body 10 is performed in the heating restart step, sleeve portions located at both end portions of the balloon can be prevented from excessively swelling in the annealing treatment for the balloon.

As shown in FIG. 1 to FIG. 5, the second production method for the balloon catheter of the present invention includes: a tubular body placement step of placing a resin tubular body 10 inside a mold 20; a mold placement step of placing the mold 20 inside a heating jacket 30; a heating start step of starting heating the heating jacket 30; an elongation start step of starting elongating the resin tubular body 10 to both sides in a lengthwise direction thereof an elongation end step of ending elongating the resin tubular body 10; and a detaching step of detaching the mold 20 from the heating jacket 30, wherein the detaching step is performed before the elongation end step. Explanations about the second production method of the present invention exclude the same explanations as those about the aforementioned first production method.

As shown in FIG. 5, the mold 20 is detached from the heating jacket 30 in the detaching step. The detaching step is performed before the elongation end step. If the detaching step is performed before the elongation end step, supply of heat to the mold 20 by the heating jacket 30 is ended during elongation of the resin tubular body 10. Thus, influence of a so-called temperature overshoot which is a phenomenon in which the actual temperature of the mold 20 exceeds the target temperature, is eliminated, and the temperature of the entire mold 20 becomes uniform owing to heat conduction of the mold 20 itself. As a result, the balloon produced with this mold 20 neither suffers variation in thickness nor is bent, and can be made as a high-quality balloon.

The detaching step is performed before the elongation end step, and the detaching step is preferably performed before the elongation start step. That is, the elongation start step and the elongation end step are preferably performed after the detaching step is performed. If the detaching step is performed before the elongation start step in the balloon production method, the temperature of the mold 20 not having yet been subjected to the elongation start step becomes entirely uniform. Thus, the mold 20 is less likely to suffer non-uniformity in temperature, and variation in thickness, bending, and the like of the balloon are less likely to occur.

It is preferable to include: a mold re-placement step of placing the mold 20 inside the heating jacket 30, the mold re-placement step being performed after the detaching step; and the heating restart step of restarting heating the heating jacket 30, the heating restart step also being performed after the detaching step. If the heating jacket 30 is heated after the detaching step to heat the mold 20 again and heat the molded balloon, annealing treatment for removing residual stress from the balloon can be performed. Therefore, the dimensional stability and the physical stability of the balloon can be improved.

In the mold re-placement step, the same heating jacket 30 as that used in the mold placement step may be used, or a different heating jacket 30 may be used. Out of the heating jackets 30, the same heating jacket 30 as that used in the mold placement step is preferably used as the heating jacket 30 to be used in the mold re-placement step. If the same heating jacket 30 as that used in the mold placement step is used in the mold re-placement step, the number of heating jackets 30 to be used in production of the balloon is one. Thus, cost for producing the balloon can be reduced.

The difference between the temperature of the heating jacket 30 at the end of the detaching step and the temperature of the heating jacket 30 at the start of the mold re-placement step is preferably not higher than 100° C. If the difference between the temperature of the heating jacket 30 at the end of the detaching step and the temperature of the heating jacket 30 at the start of the mold re-placement step is set to fall within the above range, it becomes easy to set the temperature of the mold 20 to a temperature suitable for molding a balloon when the mold re-placement step is performed and the heating restart step is performed after performing the detaching step. Therefore, production efficiency for the balloon is improved.

The difference between the temperature of the heating jacket 30 at the end of the detaching step and the temperature of the heating jacket 30 at the start of the mold re-placement step is further preferably not higher than 10° C. If the difference between the temperature of the heating jacket 30 at the end of the detaching step and the temperature of the heating jacket 30 at the start of the mold re-placement step is set to fall within the above range, the temperature of the heating jacket 30 does not need to be significantly increased for heating the mold 20 when the mold re-placement step and then the heating restart step are performed after the detaching step. As a result, the time taken to produce the balloon can be shortened, and production efficiency can be improved.

The difference between the temperature of the heating jacket 30 at the end of the detaching step and the temperature of the heating jacket 30 at the start of the mold re-placement step is preferably not higher than 10° C., more preferably not higher than 5° C., and further preferably not higher than 3° C. If the upper limit value of the difference between the temperature of the heating jacket 30 at the end of the detaching step and the temperature of the heating jacket 30 at the start of the mold re-placement step is set to fall within the above range, the difference between the temperature of the heating jacket 30 at the end of the detaching step and the temperature of the heating jacket 30 at the start of the mold re-placement step can be made small, and it is possible to shorten the time required for increasing or reducing the temperature of the heating jacket 30 to set the temperature of the mold 20 to the target temperature at the time of performing the heating restart step. As a result, the balloon can be efficiently produced. It is noted that: the difference between the temperature of the heating jacket 30 at the end of the detaching step and the temperature of the heating jacket 30 at the start of the mold re-placement step is preferably small; and the temperature of the heating jacket 30 at the end of the detaching step and the temperature of the heating jacket 30 at the start of the mold re-placement step may be equal to each other.

The mold re-placement step may be performed before the heating restart step but is preferably performed after the heating restart step. If the mold re-placement step is performed after the heating restart step, the mold re-placement step can be immediately performed from a state where the temperature of the heating jacket 30 has reached a preset value. Thus, the mold 20 can be swiftly heated again.

The heating jacket 30 preferably includes a plurality of partial heating jackets. If the heating jacket 30 includes a plurality of partial heating jackets, the heating jacket 30 can be closed by engaging the partial heating jackets with each other, and meanwhile, the heating jacket 30 can be opened by disengaging the partial heating jackets from each other. Thus, the heating jacket 30 is easily opened or closed, and it becomes easy to perform the mold placement step and the detaching step, whereby production efficiency for the balloon can be improved.

The plurality of partial heating jackets may be placed in a circumferential direction of the mold 20 or may be placed in an axial direction of the mold 20. In a case where the plurality of partial heating jackets are placed in the circumferential direction of the mold 20, the heating jacket 30 can be, for example, formed to have a structure with a half-split shape, and it becomes easy to place the mold 20 on the inner side of the heating jacket 30. In a case where the plurality of partial heating jackets are placed in the axial direction of the mold 20, the temperature of each partial heating jacket can be individually set, and the heating temperature of the mold 20 can be made different in the axial direction of the mold 20.

The heating jacket 30 includes a first partial heating jacket 31 located closer to one side surface of the mold 20 and a second partial heating jacket 32 located closer to another side surface of the mold 20. The detaching step preferably includes separating at least one of the first partial heating jacket 31 and the second partial heating jacket 32 from the mold 20. If the detaching step is performed by separating at least one of the first partial heating jacket 31 and the second partial heating jacket 32 from the mold 20, the mold 20 can be easily detached from the heating jacket 30, and production efficiency for the balloon can be improved.

Although not shown, the first partial heating jacket 31 and the second partial heating jacket 32 are preferably connected to each other via a hinge portion. If the first partial heating jacket 31 and the second partial heating jacket 32 are connected to each other via a hinge portion, opening or closing between the first partial heating jacket 31 and the second partial heating jacket 32 is easily and assuredly performed.

The first partial heating jacket 31 and the second partial heating jacket 32 may be connected to each other via a cylinder. If the first partial heating jacket 31 and the second partial heating jacket 32 are connected to each other via a cylinder, the heating jacket 30 can be opened or closed with the cylinder. Thus, an opening/closing operation of the heating jacket 30 is easily and assuredly performed, and furthermore, the force with which the first partial heating jacket 31 and the second partial heating jacket 32 are pressed against content such as the mold 20 can be controlled. Examples of the type of the cylinder include an air cylinder, a hydraulic cylinder, an electric cylinder, and the like.

Although not shown, it is also preferable that: the heating jacket 30 includes a first partial heating jacket located closer to one end of the mold 20 and a second partial heating jacket located closer to another end of the mold 20; and the detaching step includes separating at least one of the first partial heating jacket and the second partial heating jacket from the mold 20. If the heating jacket 30 includes the first partial heating jacket located closer to the one end of the mold 20 and the second partial heating jacket located closer to the other end of the mold 20 and the detaching step is performed by separating at least one of the first partial heating jacket and the second partial heating jacket from the mold 20, it becomes easy to cause the heating temperature of the mold 20 to be different in the axial direction of the mold 20.

A step of placing the mold 20 inside a cooling jacket 40 as shown in FIG. 7 is preferably further included, the step being performed after the elongation end step of ending elongating the resin tubular body 10 shown in FIG. 6. If the step of placing the mold 20 inside the cooling jacket 40 is included and the step is subsequent to the elongation end step, the mold 20 in a heated state having been subjected to the elongation end step can be swiftly cooled, and production efficiency for the balloon can be improved.

The cooling jacket 40 is used for cooling the mold 20. If the mold 20 is placed inside the cooling jacket 40 after the elongation end step, the temperature of the mold 20 heated by the heating jacket 30 for elongation of the resin tubular body 10 and the annealing treatment for the balloon can be reduced. Examples of the case of cooling the mold 20 with use of the cooling jacket 40 include: a case where a molding temperature for the balloon or a temperature for the annealing treatment is rapidly reduced to normal temperature at once; a case where the mold 20 is rapidly cooled to a temperature slightly higher than a sterilizing temperature (for example, about 45° C. to 55° C.) to remove residual stress, then the mold 20 is taken out from the cooling jacket 40 or cooling by the cooling jacket 40 is stopped to keep the mold 20 at the aforementioned temperature slightly higher than the sterilizing temperature for a certain time and remove residual stress, and then the mold 20 is placed inside the cooling jacket 40 again or cooling by the cooling jacket 40 is started to cool the mold 20 to normal temperature; and the like.

A cooling start step of starting cooling the cooling jacket 40 may be included. If the cooling start step is performed, the cooling jacket 40 can be cooled to a preset temperature in the cooling start step. Thus, the cooling jacket 40 cools the mold 20, whereby the resin tubular body 10 or the balloon placed inside the mold 20 can be sufficiently cooled.

A cooling end step of ending cooling the cooling jacket 40 may be included. Alternatively, a cooling jacket detaching step of detaching the mold 20 from the cooling jacket 40 may be included. If the cooling end step or the cooling jacket detaching step is performed, after a balloon is cooled and production thereof is completed, the process can proceed to a step of producing the next balloon. Thus, production efficiency for balloons can be improved, and balloons can be successively produced.

Similar to the heating jacket 30, the cooling jacket 40 is preferably configured to have a plurality of partial cooling jackets including a first partial cooling jacket 41 located closer to the one side surface of the mold 20 and a second partial cooling jacket 42 located closer to the other side surface of the mold 20. In addition, the first partial cooling jacket 41 and the second partial cooling jacket 42 are preferably connected to each other via a hinge portion. If the cooling jacket 40 is configured such that the first partial cooling jacket 41 and the second partial cooling jacket 42 are connected to each other via a hinge portion, it becomes easy to perform the step of placing the mold 20 inside the cooling jacket 40 and the step of detaching the mold 20 from the cooling jacket 40.

As described above, the first production method for the balloon catheter of the present invention is a method for producing a balloon catheter having a shaft extending in a distal-proximal direction and a balloon provided on a distal side of the shaft, the method including: a tubular body placement step of placing a resin tubular body inside a mold; a mold placement step of placing the mold inside a heating jacket; a heating start step of starting heating the heating jacket; an elongation start step of starting elongating the resin tubular body to both sides in a lengthwise direction thereof; an elongation end step of ending elongating the resin tubular body; and a heating end step of ending heating the heating jacket, wherein the heating end step is performed before the elongation end step. Further, the second production method for the balloon catheter of the present invention is a method for producing a balloon catheter having a shaft extending in a distal-proximal direction and a balloon provided on a distal side of the shaft, the method including: a tubular body placement step of placing a resin tubular body inside a mold; a mold placement step of placing the mold inside a heating jacket; a heating start step of starting heating the heating jacket; an elongation start step of starting elongating the resin tubular body to both sides in a lengthwise direction thereof; an elongation end step of ending elongating the resin tubular body; and a detaching step of detaching the mold from the heating jacket, wherein the detaching step is performed before the elongation end step. Since the balloon catheter production methods of the present invention include these steps, before elongation of the resin tubular body placed inside the mold to both sides in the lengthwise direction thereof is ended, heating of the heating jacket is ended or the mold is detached from the heating jacket, whereby supply of heat from the heating jacket to the mold can be ended. Consequently, the temperature of the entire mold easily becomes uniform owing to heat conduction of the mold itself. That is, the resin tubular body is elongated in a state where the temperature of the entire mold is uniform. Therefore, the resin tubular body placed inside the mold is less likely to suffer non-uniformity in temperature, whereby it is possible to mold a balloon that has a uniform thickness and that is less likely to be bent.

The present application claims the benefit of priority based on Japanese patent application number 2019-47523 filed on Mar. 14, 2019. The entire content of the specification of Japanese patent application number 2019-47523 filed on Mar. 14, 2019 is incorporated herein by reference.

DESCRIPTION OF REFERENCE SIGNS 10 resin tubular body
10a larger-thickness portion
20 mold
21 center portion mold
22 end portion mold
30 heating jacket
31 first partial heating jacket
32 second partial heating jacket
40 cooling jacket
41 first partial cooling jacket
42 second partial cooling jacket

The invention claimed is:

1. A method for producing a balloon catheter having a shaft extending in a distal-proximal direction and a balloon provided on a distal side of the shaft, the method comprising:
   a tubular body placement step of placing a resin tubular body inside a mold;
   a mold placement step of placing the mold inside a heating jacket so that the mold is heated by the heating jacket;
   a heating step of heating the heating jacket;
   an elongation start step of starting elongating the resin tubular body in a lengthwise direction thereof;
   an elongation end step of ending elongating the resin tubular body; and
   a heating end step of ending heating the heating jacket, wherein
   the heating end step is performed before the elongation end step.

2. The method for producing the balloon catheter according to claim 1, wherein the heating end step is performed before the elongation start step.

3. The method for producing the balloon catheter according to claim 1, further comprising a heating restart step of restarting heating the heating jacket, the heating restart step being performed after the heating end step.

4. A method for producing a balloon catheter having a shaft extending in a distal-proximal direction and a balloon provided on a distal side of the shaft, the method comprising:
   a tubular body placement step of placing a resin tubular body inside a mold;
   a mold placement step of placing the mold inside a heating jacket so that the mold is heated by the heating jacket;
   a heating step of heating the heating jacket;
   an elongation start step of starting elongating the resin tubular body in a lengthwise direction thereof;
   an elongation end step of ending elongating the resin tubular body; and
   a detaching step of detaching the mold from the heating jacket, wherein
   the detaching step is performed before the elongation end step.

5. The method for producing the balloon catheter according to claim 4, wherein the detaching step is performed before the elongation start step.

6. The method for producing the balloon catheter according to claim 4, further comprising:
   a mold re-placement step of placing the mold inside the heating jacket, the mold re-placement step being performed after the detaching step; and
   a heating restart step of restarting heating the heating jacket, the heating restart step also being performed after the detaching step.

7. The method for producing the balloon catheter according to claim 6, wherein a difference between a temperature of the heating jacket at an end of the detaching step and a temperature of the heating jacket at a start of the mold re-placement step is not higher than 100° C.

8. The method for producing the balloon catheter according to claim 7, wherein the difference between the temperature of the heating jacket at the end of the detaching step and the temperature of the heating jacket at the start of the mold re-placement step is not higher than 10° C.

9. The method for producing the balloon catheter according to claim 4, wherein the heating jacket comprises a plurality of partial heating jackets.

10. The method for producing the balloon catheter according to claim 9, wherein
the plurality of partial heating jackets includes
a first partial heating jacket located closer to one side surface of the mold, and
a second partial heating jacket located closer to another side surface of the mold, and
the detaching step includes separating at least one of the first partial heating jacket and the second partial heating jacket from the mold.

11. The method for producing the balloon catheter according to claim 10, wherein the first partial heating jacket and the second partial heating jacket are connected to each other via a hinge portion.

12. The method for producing the balloon catheter according to claim 9, wherein
the plurality of partial heating jackets includes
a first partial heating jacket located closer to one end of the mold, and
a second partial heating jacket located closer to another end of the mold, and
the detaching step includes separating at least one of the first partial heating jacket and the second partial heating jacket from the mold.

13. The method for producing the balloon catheter according to claim 4, wherein the heating step is started before the mold placement step.

14. The method for producing the balloon catheter according to claim 4, further comprising a step of placing the mold inside a cooling jacket, the step being performed after the elongation end step of ending elongating the resin tubular body.

15. The method for producing the balloon catheter according to claim 1, wherein the heating step is started before the mold placement step.

16. The method for producing the balloon catheter according to claim 1, further comprising a step of placing the mold inside a cooling jacket, the step being performed after the elongation end step of ending elongating the resin tubular body.

* * * * *